US012590898B2

(12) United States Patent
Nguyen et al.

(10) Patent No.: US 12,590,898 B2
(45) Date of Patent: Mar. 31, 2026

(54) SPECTROPHOTOMETRIC SYSTEM AND METHOD FOR WIRELESS WATER QUALITY MANAGEMENT OF AQUACULTURE BASIN

(71) Applicant: RYNAN TECHNOLOGIES PTE. LTD., Singapore (SG)

(72) Inventors: My T. Nguyen, Tra Vinh City (VN); Truong T. Pham, Tra Cu District (VN); Camtho T. Nguyen, Choi Moi District (VN); Tri H. Le, Cang Long District (VN); Vietthu T. Nguyen, Choi Moi District (VN); Truong N. Tran, Giong Rieng District (VN); Nam Q. Doan, Chau Phu District (VN); Dat T. Bui, Duyen Hai District (VN); Quy M. Phan, Tra Vinh City (VN); Cuong Q. Hong, Tra Vinh City (VN)

(73) Assignee: RYNAN TECHNOLOGIES PTE. LTD., Singapore (SG)

( * ) Notice: Subject to any disclaimer, the term of this patent is extended or adjusted under 35 U.S.C. 154(b) by 865 days.

(21) Appl. No.: 17/770,440

(22) PCT Filed: Apr. 13, 2021

(86) PCT No.: PCT/IB2021/053050
§ 371 (c)(1),
(2) Date: Apr. 20, 2022

(87) PCT Pub. No.: WO2022/219373
PCT Pub. Date: Oct. 20, 2022

(65) Prior Publication Data
US 2024/0027354 A1      Jan. 25, 2024

(51) Int. Cl.
*G01N 21/78* (2006.01)
*G01N 21/03* (2006.01)
(Continued)

(52) U.S. Cl.
CPC ............. *G01N 21/78* (2013.01); *G01N 21/03* (2013.01); *G01N 21/11* (2013.01); *G01N 21/31* (2013.01); *G01N 33/18* (2013.01)

(58) Field of Classification Search
CPC ........ G01N 21/78; G01N 21/11; G01N 21/31; G01N 33/18; G01N 21/03;
(Continued)

(56) References Cited

U.S. PATENT DOCUMENTS 3,475,102 A    10/1969  Larsen
3,477,822 A    11/1969  Hamilton
(Continued)

FOREIGN PATENT DOCUMENTS

CA        2198854  A1 *   3/1996   .............. B01F 33/30
CN      106872385        6/2017
(Continued)

OTHER PUBLICATIONS

Sargazi et al., "Application of a smartphone based spectrophotometer for rapid in-field determination of nitrite and chlorine in environmental water samples", Spectrochimica Acta Part A: Molecular and Biomolecular Spectroscopy, vol. 227, Oct. 19, 2019, Amsterdam, NL; 5 pages.
(Continued)

*Primary Examiner* — Maris R Kessel
*Assistant Examiner* — Valerie Simmons
(74) *Attorney, Agent, or Firm* — Wells St. John P.S.

(57) ABSTRACT

There is provided a spectrophotometric system and method for measuring the concentration of discrete water-soluble compounds or minerals in the water of a live aquaculture basin. The system comprises a portable wireless spectrophotometer with an optical code reader for automatic identification of water sample cuvettes. The cuvettes bear an optical code identifier and are preloaded with at least one
(Continued)

solid color indicating reagent dry tablet. The cuvettes are internally sized and shaped for a smaller tablet type to fall to the bottom and a larger tablet type not to not fall to the bottom and vertically rest at an intermediate height within the cuvette interior thereby creating vertical separation between the tablet types and avoiding cross-reactions or degradation while in storage or transport. The system can also include a mobile application for displaying the spectra results and for providing recommendations or e-commerce purchase means for water quality improvement.

15 Claims, 7 Drawing Sheets

(51) Int. Cl.

| | | |
|---|---|---|
| *G01N 21/11* | (2006.01) | |
| *G01N 21/31* | (2006.01) | |
| *G01N 33/18* | (2006.01) | |

(58) Field of Classification Search

CPC ... G01N 2021/0325; G01N 2021/0382; G01N 2035/00752; G01N 2035/00772; G01N 35/00732; G01N 2035/00881; G01N 2035/00891; G01N 35/00871; G01N 2201/0221; G01N 21/251; G01J 3/0256; G01J 3/0264; G01J 3/42

See application file for complete search history.

(56) References Cited

U.S. PATENT DOCUMENTS

| | | | | |
|---|---|---|---|---|
| 5,386,287 | A * | 1/1995 | Berssen | G01N 35/00732 |
| | | | | 356/414 |
| 2009/0155923 | A1 * | 6/2009 | Bonecker | B01F 35/713 |
| | | | | 436/166 |
| 2009/0298051 | A1 * | 12/2009 | Salter | C12Q 1/10 |
| | | | | 435/5 |
| 2012/0105837 | A1 * | 5/2012 | Ingber | B01L 3/508 |
| | | | | 356/244 |
| 2013/0306732 | A1 | 11/2013 | Berssen et al. | |
| 2015/0160248 | A1 * | 6/2015 | Gussakovsky ... | G01N 35/00871 |
| | | | | 235/494 |
| 2016/0069919 | A1 | 3/2016 | Holmes et al. | |
| 2016/0320381 | A1 | 11/2016 | Holmes et al. | |
| 2018/0005095 | A1 * | 1/2018 | Schindler, III | G06Q 10/083 |
| 2019/0308187 | A1 * | 10/2019 | Dagland | B01L 3/0275 |

FOREIGN PATENT DOCUMENTS

| | | |
|---|---|---|
| JP | 2016-179470 | 10/2016 |
| KR | 10-2122053 | 6/2020 |
| TW | 336735 U | 7/1998 |
| WO | WO 2010/027982 | 3/2010 |
| WO | PCT/IB2021/053050 | 12/2021 |

OTHER PUBLICATIONS

Srivastava, et al., "Smartphone-based System for water quality analysis", Applied Water Science, vol. 8, No. 5, Aug. 6, 2018, Germany; 13 pages.

* cited by examiner

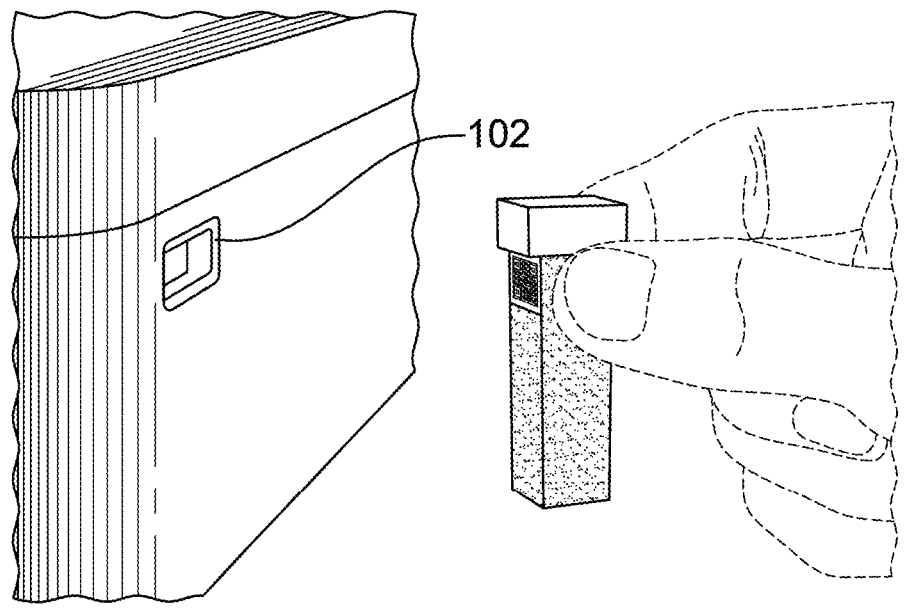
FIGURE 1C
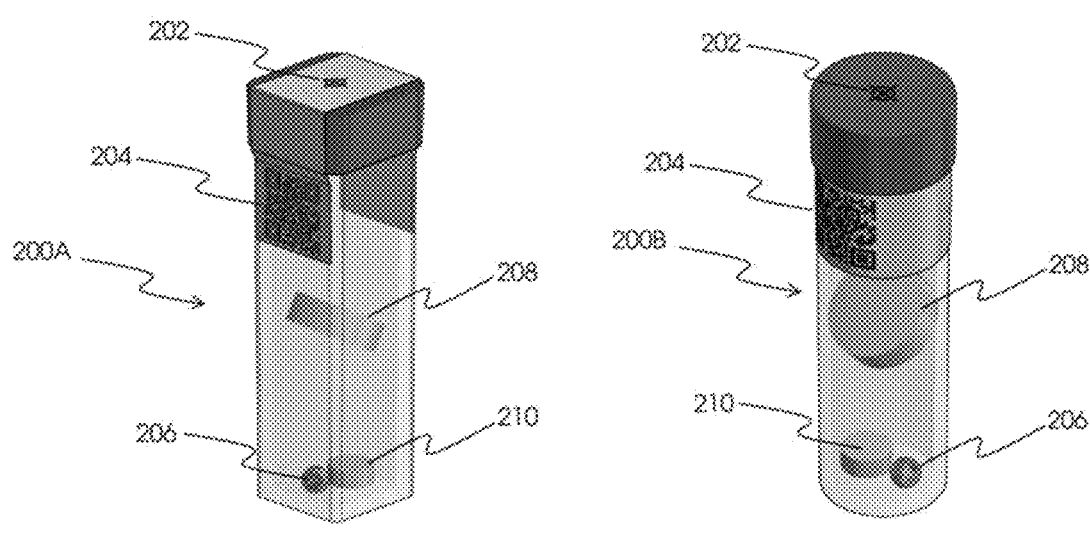
FIGURE 2A                    FIGURE 2B

SPECTROPHOTOMETRIC SYSTEM AND METHOD FOR WIRELESS WATER QUALITY MANAGEMENT OF AQUACULTURE BASIN

RELATED PATENT DATA

This application is a 35 U.S.C. § 371 of and claims priority to PCT International Application Number PCT/IB2021/053050 which was filed 13 Apr. 2021, the teachings of which are incorporated by reference herein.

FIELD OF THE INVENTION

The present invention relates to the field of monitoring of water quality in aquaculture operations. More specifically the present invention relates to a wireless system for spectrophotometric monitoring of water quality.

BACKGROUND

In intensive and super intensive aquaculture, around 35% of the nitrogen in the protein of feeds applied to aquaculture basins is recovered in harvest biomass. However, the remaining 60% or so remains in the water in the form of uneaten feed and feces or is excreted as ammonia nitrogen by aquatic animals or microorganisms present in the water. Protein in uneaten feed and feces is converted by bacteria and other decomposer organisms into ammonia ($NH_3$), ammonium cation ($NH_4^+$), nitrite ($NO_2^-$) and nitrate ($NO_3^-$) compounds. These compounds when present in higher concentrations will have a deleterious effect on the growth and health of the aquatic species being raised. Therefore, water quality must be regularly monitored, especially for the presence of nitrogen compounds or other contaminants. Depending on this monitoring, remedial measures may be taken to address bad water quality situations.

The concentrations of these nitrogen compounds or other contaminants in the water will vary depending on number of many factors, such as the biomass of aquatic animals in a given aquaculture basin, the amount of applied feed, the microbial and phytoplankton populations, water temperature, dissolved oxygen, weather conditions and others.

Different types of physical devices have been used to quantitatively monitor nitrogen compounds or other contaminants in aquaculture basins offline or in real time, such as voltametric sensors, polarographic sensors, optical sensors, and ion selective sensors. However, these are expensive equipment that require intensive maintenance and calibrations to ensure accurate results. In most circumstances, their useful operating life is relatively short and such equipment normally needs to be replaced every few months.

Colorimetry is a chemical method, which is used to quickly and economically determine the concentration of a given nitrogen compound in water of aquaculture ponds using liquid or solid color indicators. These are usually supplied as test kits by manufactures in small plastic bottles or tablets. Different color indicating reagents are used for identifying different nitrogen compounds. In practice, a water sample is manually collected using a plastic container with a predetermined liquid volume. The instructed number of drops or tablets of the color indicator reagents are added into the water sample container. As the reagents react with the nitrogen compound to be identified, the aqueous solution changes color with different intensity depending on the concentration of the nitrogen compound or minerals in water. The concentration of a nitrogen compound is visually estimated by comparing the color intensity of the aqueous solution with a standardized color chart. This technique produces low accuracy results.

Spectrophotometers have been used to record the absorbance of an aqueous solution at wavelengths. The concentration of nitrogen compounds or other contaminants in the water samples of aquaculture basins such as shrimp ponds are determined by comparison with data of the absorbances of the water solutions containing known concentration of nitrogen or other compounds of interest. Such equipment provides more accurate results than colorimetry.

Thus, the concentration of soluble inorganic compounds containing phosphate, nitrogen, calcium, sulfur, magnesium, and other minerals present in the water of aquaculture ponds or vessels can be determined by using spectrophotometric method with various commercially available color indicator reagents.

Often, spectrophotometric tests require more than one reagent present in a sample cuvette. When in solid form such as pellets or tablets, reagents are generally already present in a sample cuvette, awaiting water samples to be mixed therein and tested. One drawback of indicator reagents is that when in solid form in the same container or cuvette some indicator reagents would cross-react while in storage or transportation thereby affecting the accuracy of later water sample tests.

It would be advantageous to provide container or cuvettes with predetermined reagents that will not cross-react while in storage or transportation.

It would be advantageous to provide a wireless system for convenient water quality monitoring that is simple to use and that provides accurate water quality information.

It would also be advantageous to provide a wireless system that provides records of water quality readings so as to provide historical data and traceability of the growing conditions of a given aquaculture basin.

It would also be advantageous to provide a system that provides a smartphone, tablet or computer application providing real-time water quality analysis results and that can further comprise e-commerce capabilities responsive to requirements for aquaculture feed, chemicals, or additives so as to remedy water quality issues.

In another aspect it would also be advantageous to improve the traceability of aquaculture harvests by recording and providing the provenance and growth conditions of the aquatic species including water quality, feed and additives. For example, from a shrimp grow out basin at larvae stage all the way to the point of sale of mature shrimp anywhere in the world. Full traceability means that consumers and retailers may trace back the provenance and aquaculture conditions such as location of the grow out basin, feed manufacturer, production location, feed ingredients, medications used, if any, yield of harvest including size of aquatic species over time, harvest date, expiry date, feeding times, feeding conditions, water quality conditions, harvest storage conditions and distribution routes.

SUMMARY

In one embodiment this invention relates to an internet connected spectrophotometric system and methods for measuring and recording water quality by quantitative (concentration) determination water soluble compounds containing nitrogen, sulfur, phosphor, calcium, magnesium, and other minerals in water for aquaculture farming.

In an embodiment there is provided a spectrophotometric system comprising a portable wireless spectrophotometer connected to the internet via 3G, 4G, 5G, WIFI and/or Bluetooth, the spectrophotometer comprising an optical code reader for automatic identification of water sample cuvettes, a light source and detector for measuring absorbance through water sample cuvettes, display means for displaying user interfaces or absorbance spectra results, communication means for communicating measurement data to a network, the spectrophotometric system comprising:

Sample cuvettes bearing an optical code identifier and preloaded with at least one solid color indicating reagent tablet and optionally preloaded with at least one mixing ball to mix water samples and the color indicating reagents tablet(s);

The sample cuvettes being internally sized and shaped so that a first smaller tablet type and size can fall to the bottom of the cuvette and a larger tablet type and size can be placed in the cuvette but not fall to the bottom and come to rest at an intermediate height within the cuvette interior thereby creating physical vertical separation between the tablet types and avoiding contact and cross-reactions or degradation while in storage or transport;

A mobile application having piggybacked e-commerce means for ordering water adjustment products and services;

A software as a service for displaying and analyzing the data, which are recorded by the spectrophotometer.

In an embodiment, the method for determination of water-soluble compounds containing nitrogen, sulfur, phosphor, calcium, magnesium, and other minerals in water of this invention comprises the following steps:

Scanning the geoidentified optical code of the location of the aquaculture basins where water samples are collected for analysis using the mobile application, which is installed on a computerized device such as a smartphone;

Using a wireless spectrophotometer provided with an optical code scanner so as to scan the optical code on a sample cuvette thereby establishing the identity of the compound or mineral being tested for;

Obtaining a water sample from the aquaculture basin;

Filling the cuvette comprising at least one color indicating tablet with the water sample from the aquaculture basins, preferably using a syringe;

Shaking gently the sample cuvette to dissolve the at least one color indicating tablet into the water sample to generate a colored solution;

Placing the colored water sample cuvette in a sample holder of the spectrophotometer to record the absorbance spectrum between 340 and 890 nm;

Displaying the absorbance spectrum on the screen of the spectrophotometer;

Wirelessly and automatically uploading the spectrophotometer absorbance data to a remote server or to a handheld computing device such as a smartphone;

Obtaining traceability data from the water quality measurements.

BRIEF DESCRIPTION OF THE FIGURES

FIGS. 1A, 1B and 1C show the internet connected spectrophotometric system of this invention;

FIGS. 2A and 2B shows the disposable square and round cuvettes in accordance with the invention;

DESCRIPTION

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

The system of the present invention comprises a smartphone or other mobile communication device, a wireless spectrophotometer and barcoded cuvettes containing one or more reagents that will react and change color based on the concentration of compounds being found in water samples. In a preferred embodiment, the aquaculture basin is a shrimp grow out pond.

In practice, the system provides real-time water analysis and aquaculture traceability as follows. Each aquaculture basin is provided with an identifying tag, usually in the form of a unique bar code or QR code visible on a post immediately adjacent to the basin. A smartphone or other mobile device can be used to scan the code and obtain unique identifier of the basin with geopositioning coordinates. This can initiate the sequence of water quality testing of a given basin. To test the water, a sample is drawn from the basin. With a syringe of like device, the water sample is drawn into the syringe and released in sample cuvettes up to a predetermined fill line, each cuvette having pre-loaded reagents for colorimetric reactions and detection. Once filled, a cuvette is shaken to mix the contents and allow a full reaction with the reagents. Each cuvette is provided with a predetermined barcode or similar identifier.

The Wireless Spectrophotometer:

The wireless spectrophotometer of this invention has a light source (specify what type, i.e., Xenon) and detection wavelength preferably between 340 and 890 nm. It comprises a barcode reader for automatic identification of the sample cuvette comprising colored water solution. The spectrophotometer is connected to the internet via 3G, 4G, 5G or WIFI. It can also be connected to the internet via Bluetooth through a smartphone.

Figure 1A:
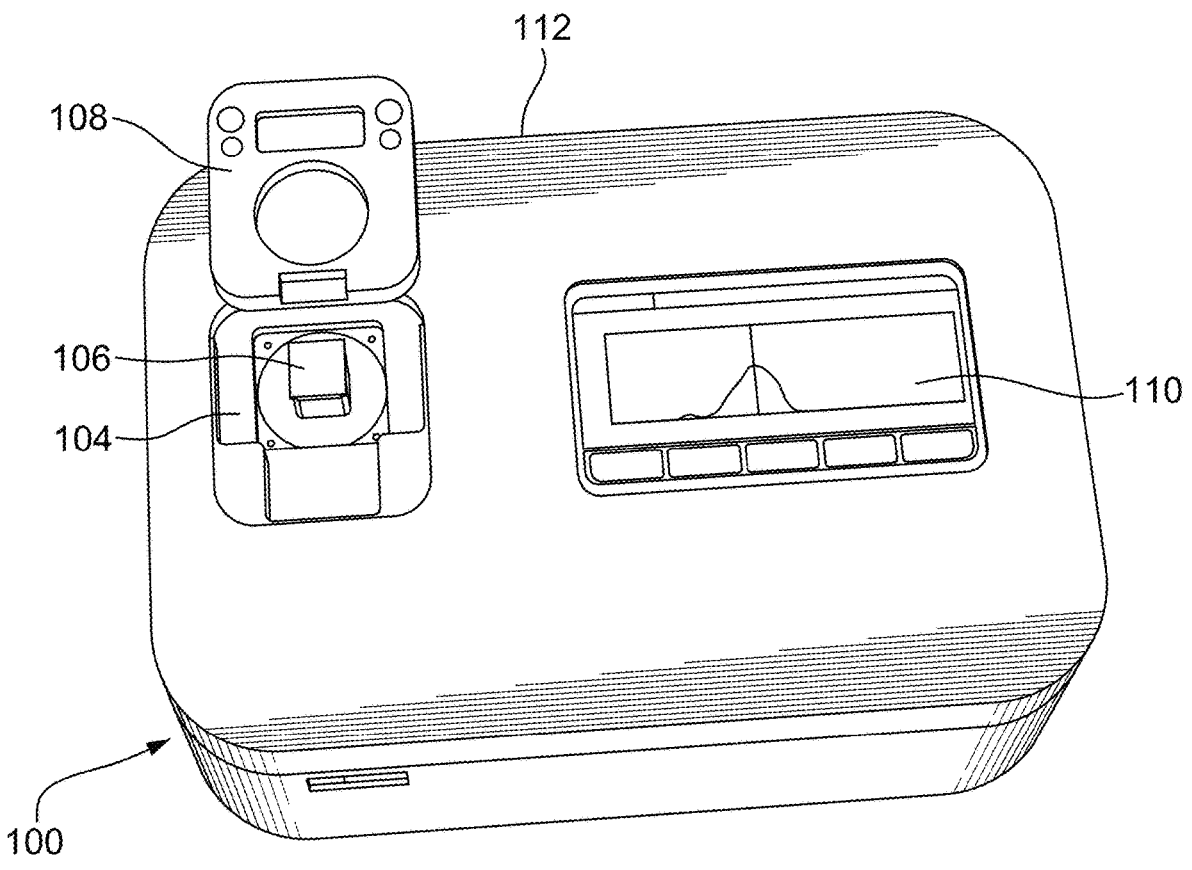
Figure 1B:
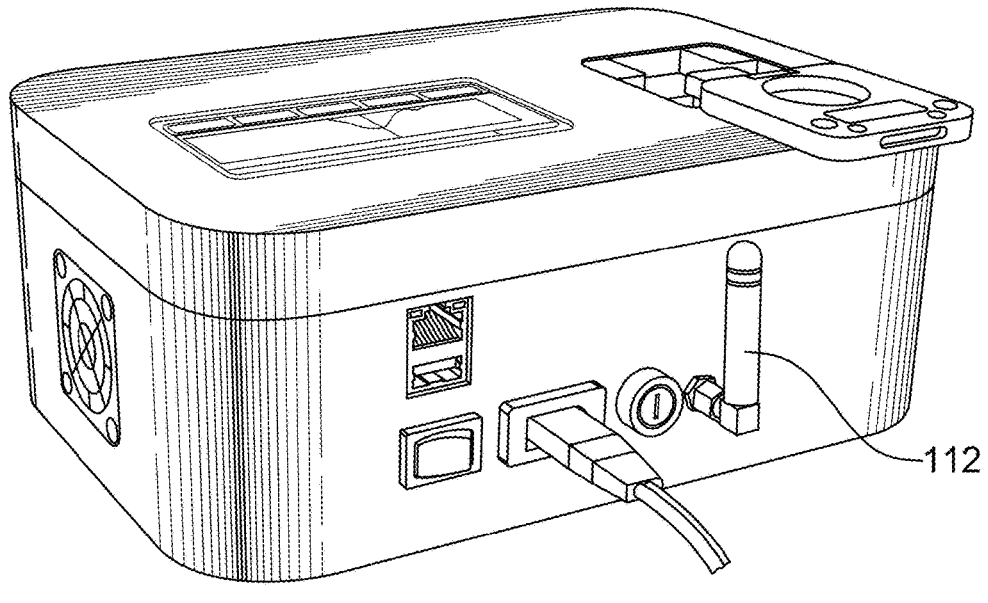

Referring now to FIGS. 1A, 1B and 10, there is shown the internet connected spectrophotometric system invention. 100 is the spectrophotometer in accordance with an embodiment of the invention. 102 shows the optical code reader that is operatively linked to the central processing unit of the spectrophotometer. 104 is the analysis chamber where a sample cuvette is placed for analysis. 106 is the sample cuvette (referred to as 200A and 200B in FIGS. 2A and 2B). 108 is the analysis chamber lid which is closed during analysis. 110 is an operating touch screen to control the spectrophotometer and launch barcode reading, sample analysis or other tasks. 112 is an antenna used to wirelessly connect to the internet.

Disposable Sample Cuvettes:

Referring now to FIGS. 2A and 2B, there is shown the disposable square and round cuvettes 200A and 200B according to an embodiment.

The preferred sample cuvettes 200A and 200B are made of transparent plastic in a tubular shape such as square or round. The cuvettes 200A and 200B are provided with a QR code 204 or similar optically or otherwise detectable identifier for automatic detection by the spectrophotometer when the cuvette 200A or 200B is placed in the optical code reader 102 and/or in chamber 104. The cuvettes 200A and 200B are preloaded with solid reagents in the form of color indicating tablets having different sizes. It is to be understood that tablets can have various shapes such as disks, ovoids, spheres, pyramids and so on. The significance of the different tablet sizes will be explained below. For efficient mixing after inserting water samples in the cuvettes, the cuvettes can also be preloaded with at least one metal, ceramic or plastic mixing ball 206. The cuvette has a fill line (not shown) for a water sample to be tested.

The cuvette is advantageously shaped and configured so that their bottom inner area 8 is smaller than the top inner area 120. This allows to separate the larger tablets from the smaller tablets so that these will not touch and cross-react during storage or transportation. The cuvettes 200A and 200B are sized and shaped so that a first smaller tablet type 210 can fall to the bottom of the cuvette and a larger tablet type 208 can be placed in the cuvette but not fall to the bottom of the cuvette thereby creating physical separation between the tablet types. The disposable sample cuvette is tightly sealed with plastic or rubber caps for transportation and storage and for holding water samples. The caps have a syringe sample injection hole 202 at their center top surface for injecting water samples therein.

In operation, a number of water tests can be performed by sequentially analyzing sample cuvettes 200A and 200B. Results can be advantageously displayed in near real-time fashion on a smartphone, tablet or computer, referred collectively as mobile communication devices, wirelessly or otherwise linked to the spectrophotometer 100.

The results of the water quality testing can thus provide useful and critical information on the concentration of soluble inorganic compounds containing phosphate, nitrogen, calcium, sulfur, magnesium, and other minerals present in the water of aquaculture basin. For example, as shown in FIGS. 3A-3C, 4A-4B, 5A-5B, 6A-6C and 7A-7C, the sample cuvettes can be used to measure the concentration of ammonia, nitrate, nitrite, hydrogen sulfide and phosphate. Thus, these figures show the sample cuvettes before and after water sample testing and the respective resulting spectra of the colored solutions. Before testing, the sample cuvettes shown in FIGS. 3A, 4A, 5A, 6A and 7A, respectively show the reagent tablets 208, 210 and mixing ball 206. Once the water samples are conducted and the cuvettes are thoroughly mixed, see FIGS. 3B, 4B, 5B, 6B and 7B, the color and absorbance can be measured by spectrophotometer 100.

FIGS. 3C, 4C, 5C, 6C and 7C present the spectra results for the various tests of Examples 1 to 5 described hereinbelow. These results are visible on the spectrophotometer display screen or mobile communication device. These results are input into an electronic processor having artificial intelligence as described below and used to generate remedial recommendations to preserve or improve water quality such as feed composition, volume and frequency, oxygen, agitation or temperature adjustments, addition of chemicals or non-chemical additives and so on.

In a preferred embodiment, a smartphone, tablet or computer application will display results and emit recommendations. Still in a preferred embodiment, the recommendations can be quickly implemented when the application is provided with an e-commerce platform for rapid purchase and delivery of recommended goods or products. The e-commerce platform may be hosted on a server and be accessible on a website or other software accessible by users.

Thus, the smartphone, tablet or computer application is communicatively coupled to software to receive spectrophotometric data of the water sample, said data being compiled by the mobile device or transmitted to a network for remote processing and relay back to the mobile device. The water quality data is compiled over time and is used to provide recommendations to the user. For example, if the water contains to many nitriles, the feed can be adjusted, or water additives may be recommended.

In an embodiment the spectrophotometric system comprises a processor linked to a network having access to a set of machine learning algorithms (MLAs) trained to determine the water quality and health parameters of the aquatic species being grown by virtue of spectrophotometric data and comparison with preferred values. To achieve that objective, the MLAs undergo a training routine based on historical data of water quality parameters as described above, as well as other known parameters from the literature or input by operators.

Thus, the set of machine learning algorithms (MLAs) is trained to determine the expected water quality patterns over time and health parameters of the aquatic species being grown and having been trained to provide a recommended course of action in response to the water quality parameters. Recommended directives can range from feed adjustments to water treatment chemicals to additives such as antivirals or antibiotics or probiotics. It will be appreciated that for each spectrophotometric parameter being measured, the aquatic species in the aquaculture basin may have a given range of tolerance or optimum health range that may vary upon the species, its maturity, and other parameters such as water temperature, salinity, turbidity, dissolved oxygen and so on. The MLAs are trained to provide recommendations taking into account a plurality of variables.

In one or more embodiments of the present technology, the network processor or mobile device can be operatively linked to equipment that is activated to implement said directives either automatically or by user input. In some embodiments, the mobile device is linked to an e-commerce platform so that the user can directly order and purchase products and have these delivered to the aquaculture basin.

Furthermore, traceability of the entire operation and system is facilitated by recording in the network of mobile application all testing data over time thereby providing historical data and recording the purchases of recommended goods or products. In an embodiment, the present technology provides water quality data access to aquaculture farmers, distributors, and customers. Thus, eventual purchasers of a given harvest of aquatic species can monitor water and obtain traceability on orders.

EXAMPLES OF CUVETTES COMPRISING SOLID COLOR INDICATING TABLETS AND FILLED WITH WATER FROM AQUACULTURE BASINS

The following are examples of water quality testing for the presence of various contaminants, compounds, or minerals. These examples are for illustration purposes.

Example 1: Cuvette with One Color Indicating Tablet for Nitrile

Comprising Only One Solid Tablet

| Size and Weight | TABLET |
| --- | --- |
| Diameter (mm) | 6.00 |
| Thickness (mm) | 3.00 |
| Weight (mg) | 200 |

The composition is in the below table

| Compositions | % |
| --- | --- |
| N-(1-naphthyl)ethylene diamine dihydrochloride | 4.00 |
| Sulfanilic acid | 8.00 |
| Potassium hydrogen sulfate | 10.00 |
| Sodium chloride | 78.00 |

Figures 3A, 3B:
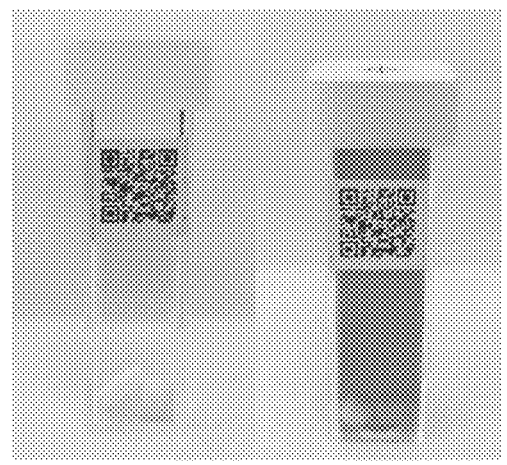
FIGS. 3A, 3B and 3C show the cuvettes before and after water sample testing and the resulting spectrum, respectively, when testing for nitrile in accordance with Example 1, herein.

Referring to FIG. 3A, the

Left—Cuvette comprises solid color indicating tablet and a ceramic mixing ball. and in FIG. 3B, Right—Cuvette is filled with water from aquaculture basin.

Figure 3C:
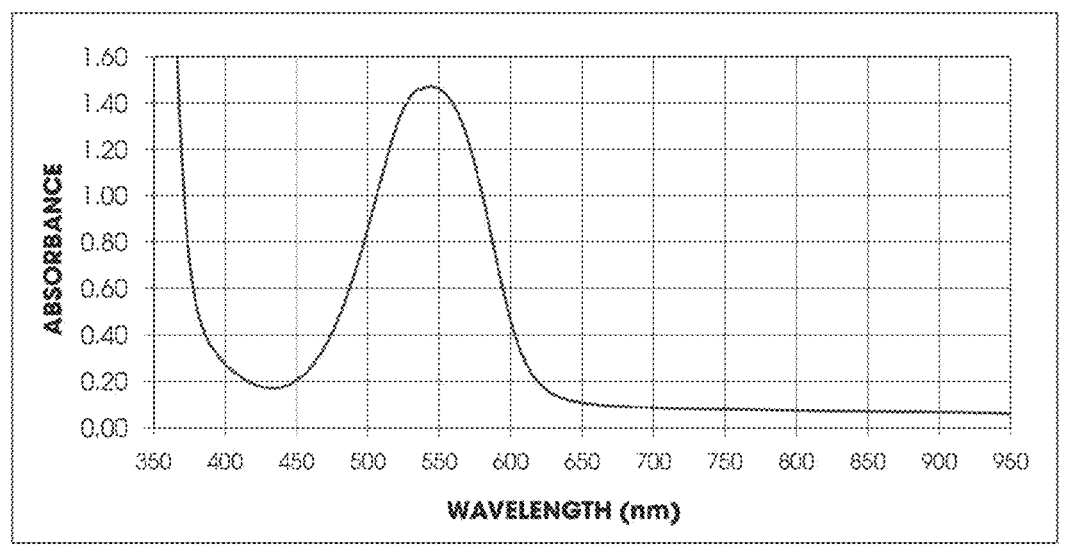

Referring to FIG. 3C, the concentration of Nitrile is 6.80 ppm and Max. Abs. is 544 nm.

Example 2: Cuvette with Two Color Indicating Tablets for Ammonia

Comprising Two Solid Color Indicating Tablets

| Size and Weight | TABLET 1 | TABLET 2 |
| --- | --- | --- |
| Diameter (mm) | 10.2 | 10.4 |
| Thickness (mm) | 3.0 | 3.5 |
| Weight (mg) | 320 | 500 |

The compositions of the solid color indication tablets are in the below table

| | Compositions | % |
| --- | --- | --- |
| Tablet 1 | Sodium salicylate | 12.500 |
| | Trisodium citrate | 33.125 |
| | Sodium nitroprusside dihydrate | 1.250 |
| | Sorbitol | 40.625 |
| | Sodium chloride | 12.500 |

8

-continued

| | Compositions | % |
| --- | --- | --- |
| Tablet 2 | Sodium hydroxide | 18.600 |
| | Sodium dichloroisocyanurate | 1.400 |
| | Sodium chloride | 58.000 |
| | Sodium acetate | 2.000 |
| | Trisodium citrate | 6.000 |
| | Sodium gluconate | 14.00 |

Figures 4A, 4B:
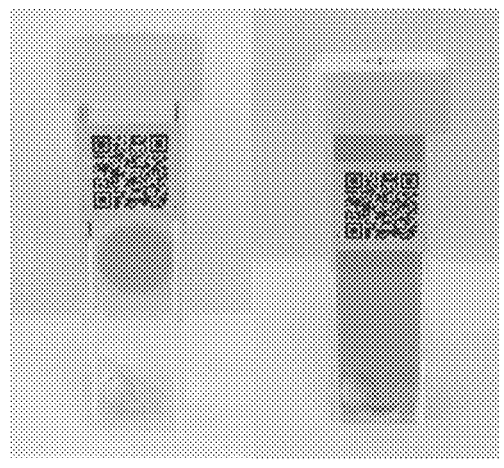
FIGS. 4A, 4B and 4C show the cuvettes before and after water sample testing and the resulting spectrum, respectively, when testing for nitrile in accordance with Example 2, herein.

Referring to FIG. 4A, the

Left—Cuvette comprises two solid color indicating tablets and a ceramic mixing ball. and in FIG. 4B, Right—Cuvette is filled with water from aquaculture basin.

Figure 4C:
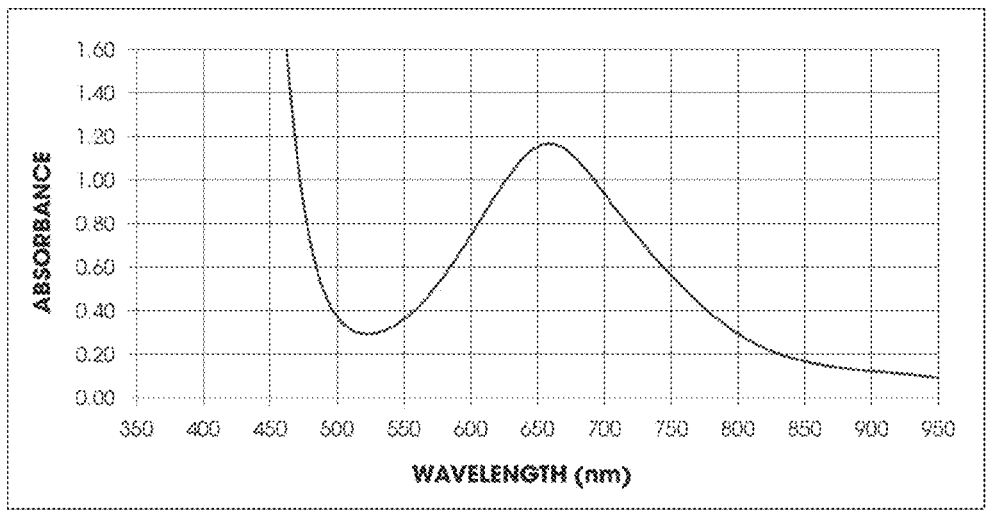

Referring to FIG. 4C, the concentration of Ammonia is 3.20 ppm and Max. Abs. is 659 nm.

Example 3: Cuvette with Two Color Indicating Tablets for Nitrate

Comprising Two Solid Color Indicating Tablets

| Size and Weight | TABLET 1 | TABLET 2 |
| --- | --- | --- |
| Diameter (mm) | 10.4 | 6.00 |
| Thickness (mm) | 1.80 | 2.00 |
| Weight (mg) | 300 | 100 |

The compositions of the solid color indication tablets are in the below table

| | Compositions | % |
| --- | --- | --- |
| Tablet 1 | N-(1-naphthyl)ethylene diamine dihydrochloride | 1.330 |
| | Sulfanilic acid | 2.670 |
| | Zinc powder | 1.330 |
| | Devarda's alloy | 0.670 |
| | Sodium chloride | 94.00 |
| Tablet 2 | Potassium hydrogen sulfate | 10.00 |
| | Ethylenediaminotetraacetic acid (tetrasodium salt) | 45.00 |
| | Ammonium chloride | 45.00 |

Figures 5A, 5B:
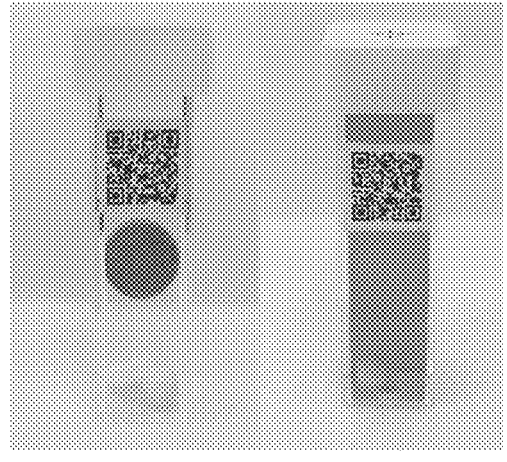
FIGS. 5A, 5B and 5C show the cuvettes before and after water sample testing and the resulting spectrum, respectively, when testing for nitrile in accordance with Example 3, herein.

Referring to FIG. 5A, the

Left—Cuvette comprises two solid color indicating tablets and a ceramic mixing ball. and in FIG. 5B, Right—Cuvette is filled with water from aquaculture basin.

Figure 5C:
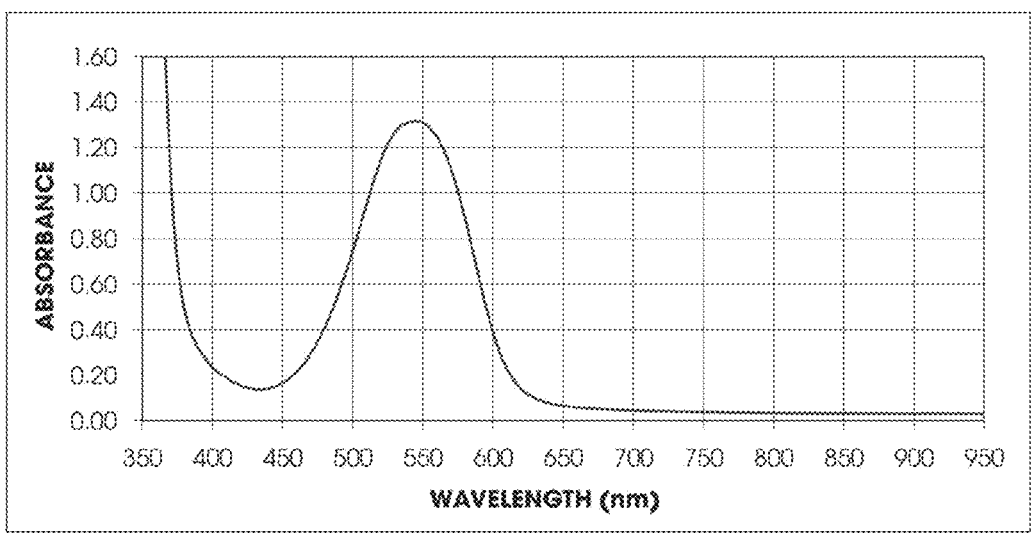

Referring to FIG. 5C, the concentration of Nitrate is 5.80 ppm and Max. Abs. is 548 nm.

Example 4: Cuvette with Two Color Indicating Tablets for $H_2S$

Comprising Two Solid Color Indicating Tablets

| Size and Weight | TABLET 1 | TABLET 2 |
| --- | --- | --- |
| Diameter (mm) | 10.4 | 6.00 |
| Thickness (mm) | 2.00 | 2.00 |
| Weight (mg) | 250 | 130 |

The compositions of the solid color indication tablets are in the below table

| | Compositions | % |
|---|---|---|
| Tablet 1 | Potassium hydrogen sulfate | 25.00 |
| | Adipic acid | 10.00 |
| | N,N-Diethyl-1,4-phenylenediammonium sulfate | 0.700 |
| | Boric acid | 32.50 |
| | Sodium chloride | 6.800 |
| | Poly ethylene glycol (PEG) | 25.00 |
| Tablet 2 | Potassium dichromate | 0.200 |
| | Sodium chloride | 66.47 |
| | Boric acid | 13.30 |
| | Poly ethylene glycol (PEG) | 20.00 |

Figures 6A, 6B:
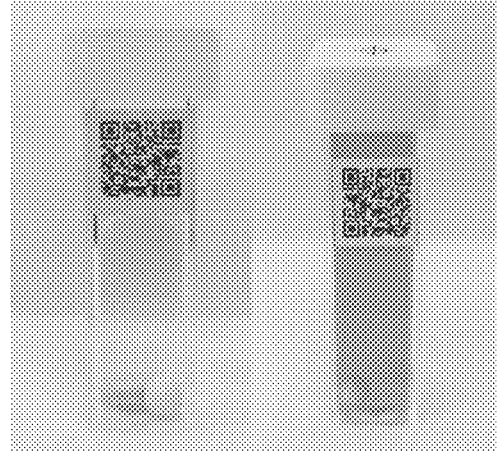
FIGS. 6A, 6B and 6C show the cuvettes before and after water sample testing and the resulting spectrum, respectively, when testing for nitrile in accordance with Example 4, herein.

Referring to FIG. 6A, the

Left—Cuvette comprises two solid color indicating tablets and a ceramic mixing ball. and in FIG. 6B, Right—Cuvette is filled with water from aquaculture basin.

Figure 6C:
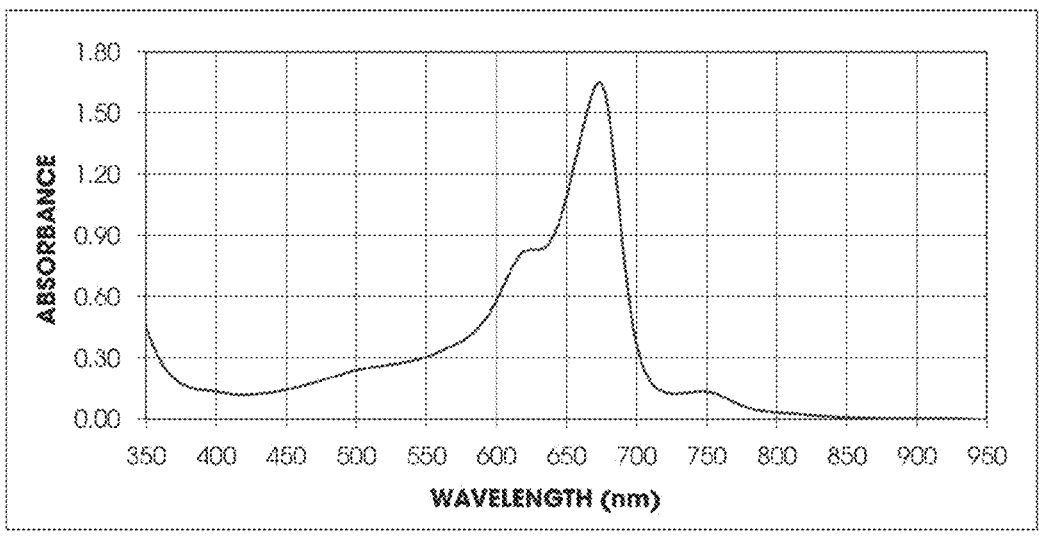

Referring to FIG. 6C, the concentration of Hydrogen sulphide is 1.40 ppm and Max. Abs. is 889 nm.

Example 5: Cuvette with Three Color Indicating Tablets for Phosphate

Comprising 3 Solid Color Indicating Tablets

| Size and Weight | Table 1 | Table 2 | Table 3 |
|---|---|---|---|
| Diameter (mm) | 10.4 | 6.00 | 10.2 |
| Thickness (mm) | 1.80 | 1.80 | 1.60 |
| Weight (mg) | 180 | 100 | 180 |

The compositions of the solid color indication tablets are in the below table

| | Compositions | % |
|---|---|---|
| Tablet 1 | Potassium hydrogen sulfate | 50.00 |
| | Adipic acid | 11.11 |
| | Boric acid | 38.89 |
| Tablet 2 | Ammonium heptamolybdate tetrahydrate | 3.000 |
| | Sodium chloride | 8.000 |
| | Boric acid | 9.000 |
| | Sodium pyrosulfite | 80.00 |
| Tablet 3 | Ascorbic acid | 2.500 |
| | Potassium antimony (III) oxide tartrate trihydrate | 0.083 |
| | Sodium chloride | 11.31 |
| | Boric acid | 19.44 |
| | Sucrose | 66.67 |

Figures 7A, 7B:
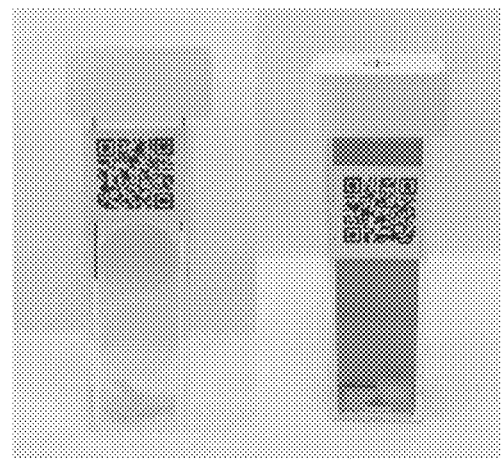
FIGS. 7A, 7B and 7C show the cuvettes before and after water sample testing and the resulting spectrum, respectively, when testing for nitrile in accordance with Example 5, herein.

Referring to FIG. 7A, the

Left—Cuvette comprises three solid color indicating tablets and a ceramic mixing ball.

and in FIG. 7B,

Right—Cuvette is filled with water from aquaculture basin.

Figure 7C:
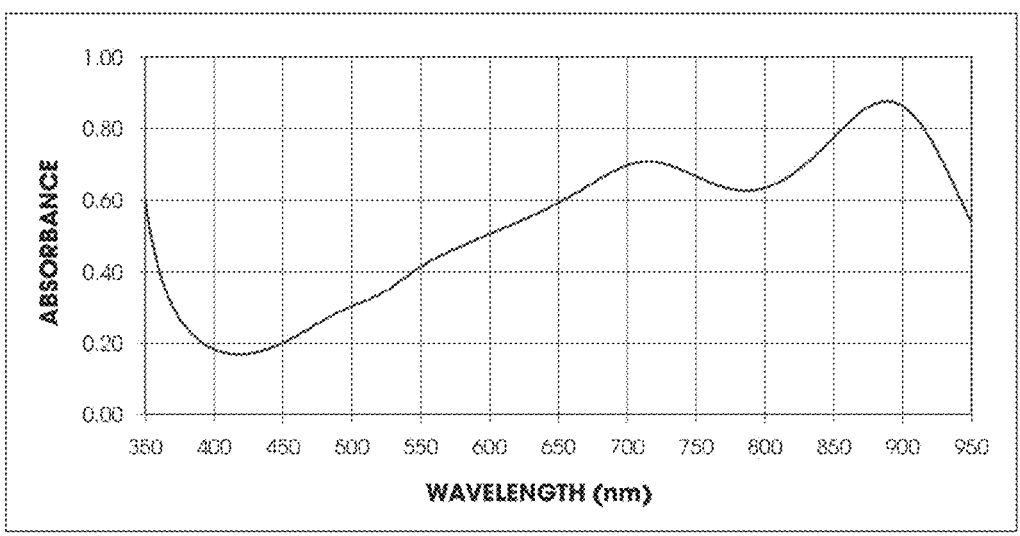

Referring to FIG. 7C, the concentration of Phosphate is is 1.20 ppm and Max. Abs. is 673 nm.

The above examples are provided for illustration and ease of comprehension and should not be interpreted as delineating the present invention. Modifications and improvements to the above-described implementations of the present technology may become apparent to those skilled in the art. Thus, the foregoing description, including the examples, is intended to be exemplary rather than limiting.

What is claimed is:

1. A sample cuvette for use with a spectrophotometer system, the sample cuvette containing and storing at least two tablets, the at least two tablets comprising at least one larger solid color indicating reagent dry tablet and at least one smaller solid color indicating reagent dry tablet, the sample cuvette comprising:

at least one side wall extending from a bottom wall at a bottom end to a top end along an axial axis, the at least one side wall and the bottom wall defining a chamber, the chamber being configured to receive the at least one larger solid color indicating reagent dry tablet and the at least one smaller solid color indicating reagent dry tablet, the chamber having:

a top radial area at the top end of the chamber being larger than the at least two tablets, a bottom radial area at the bottom end of the chamber and an intermediate radial area located between the top end and the bottom end, the intermediate radial area being larger than the at least one smaller tablet and smaller than the at least one larger tablet, thereby preventing migration of the at least one larger tablet to the bottom end and thereby creating physical vertical separation and avoiding contact between the at least one larger tablet and the at least one smaller tablet.

2. The sample cuvette of claim 1 further comprising one or more mixing balls.

3. The sample cuvette of claim 2, wherein one or more of the mixing balls are plastic.

4. The sample cuvette of claim 2, wherein one or more of the mixing balls are ceramic.

5. The sample cuvette of claim 2, wherein one or more of the mixing balls are metallic.

6. The sample cuvette of claim 1, comprising 4 side walls, the 4 side walls defining a squared bottom, top, and intermediate radial areas.

7. The sample cuvette of claim 1, wherein the sample cuvette further comprises a pierced or pierceable cap.

8. The sample cuvette of claim 7, wherein the cap is fixed.

9. A spectrophotometric system for measuring the concentration of discrete water-soluble compounds or minerals in a water of a live aquaculture basin, said system comprising a portable wireless spectrophotometer wirelessly connected to the internet via a mobile device or network, the system comprising:

at least one cuvette bearing an optical code identifier, the at least one cuvette containing and storing at least two tablets, the at least two tablets comprising at least one larger solid color indicating reagent dry tablet and at least one smaller solid color indicating reagent dry tablet, the at least one cuvette comprising:

at least one side wall extending from a bottom wall at a bottom end to a top end along an axial axis, the at least one side wall and the bottom wall defining a chamber, the chamber being configured to receive the at least one larger solid color indicating reagent dry tablet and the at least one smaller solid color indicating reagent dry tablet, the chamber having:

a top radial area at the top end of the chamber being larger than the least two tablets, a bottom radial area at the bottom end of the chamber and an intermediate radial area located between the top end and the bottom end, the intermediate radial area being larger than the at least one smaller tablet and smaller than the at least one larger tablet, thereby preventing migration of the at least one larger tablet to the bottom end and thereby creating physical vertical separation and avoiding contact between the at least one larger tablet and the at least one smaller tablet;

an optical code reader for automatic identification of the at least one cuvette;

a light source and detector for measuring absorbance through the at least one cuvette;

a processor for computing absorbance spectra results;

display means for displaying user interfaces;

communication means for communicating measurement data to a mobile device or network; and a mobile application having software as a service for displaying and analyzing the spectra results measured by the spectrophotometer and for providing remedial recommendations for water quality improvement.

10. The spectrophotometric system according to claim 9, wherein the mobile application further comprises e-commerce means for ordering water quality improvement products or services.

11. The spectrophotometric system according to claim 9, wherein said display means also provides spectra results and concentration results.

12. The spectrophotometric system according to claim 9, wherein said at least one cuvette is also preloaded with at least one mixing ball to mix water samples and the color indicating reagents tablets.

13. A method for quantitative determination of discrete water-soluble compounds or other minerals in water contained in a live aquaculture basin, said method comprising the steps of:

using a mobile computerized communication device to scan a geoidentified optical code or electronic beacon of the location of the aquaculture basin, said optical code or electronic beacon being located at or near the aquaculture basin;

using a wireless spectrophotometer provided with an optical code scanner so as to scan an optical code on a sample cuvette, thereby establishing the identity of the discrete water-soluble compound or mineral being tested for, wherein the cuvette bears an optical code identifier, the cuvette containing and storing at least two tablets, the at least two tablets comprising at least one larger solid color indicating reagent dry tablet and at least one smaller solid color indicating reagent dry tablet, the cuvette comprising:

at least one side wall extending from a bottom wall at a bottom end to a top end along an axial axis, the at least one side wall and the bottom wall defining a chamber, the chamber being configured to receive at the least one larger solid color indicating reagent dry tablet and the at least one smaller solid color indicating reagent dry tablet, the chamber having:

a top radial area at the top end of the chamber being larger than the least two tablets, a bottom radial area at the bottom end of the chamber and an intermediate radial area located between the top end and the bottom end, the intermediate radial area being larger than the at least one smaller tablet and smaller than the at least one larger tablet, thereby preventing migration of the at least one larger tablet to the bottom end and thereby creating physical vertical separation and avoiding contact between the at least one larger tablet and the at least one smaller tablet;

obtaining a water sample from the aquaculture basin;

filling the sample cuvette with the water sample from the aquaculture basin;

dissolving the at least two color indicating tablets in the sample cuvette to generate a colored solution;

placing the sample cuvette in a sample holder of the spectrophotometer and recording the absorbance spectrum;

causing the absorbance spectrum to be displayed on the screen of the spectrophotometer or on the mobile computerized communication device via wireless communication between the mobile computerized communication device and the spectrophotometer and causing the concentration of the discrete water-soluble compound or mineral to be displayed on the screen of the spectrophotometer or on the mobile computerized communication device.

14. The spectrophotometric system according to claim 13, wherein filling of the sample cuvette is completed by expelling the contents of a syringe that has itself been filled by aspiration of water from the aquaculture basin.

15. The spectrophotometric system according to claim 13, wherein the absorbance spectrum is measured between 340 nm and 890 nm.

* * * * *